United States Patent [19]

Meilland

[11] Patent Number: Plant 7,361

[45] Date of Patent: Oct. 23, 1990

[54] ROSE PLANT — MEISELGRA VARIETY

[75] Inventor: Alain A. Meilland, Antibes, France

[73] Assignee: The Conard-Pyle Company, West Grove, Pa.

[21] Appl. No.: 406,600

[22] Filed: Sep. 13, 1989

[51] Int. Cl.[5] ..... A01H 5/00

[52] U.S. Cl. ..... Plt./9

[58] Field of Search ..... Plt. 9

*Primary Examiner*—James R. Feyrer

*Attorney, Agent, or Firm*—Burns, Doane, Swecker & Mathis

[57] ABSTRACT

A new and distinct variety of rose plant of the Miniature Class is provided which forms abundantly and continuously attractive long lasting double blossoms. The blossoms are rose bengal in coloration. The plant is bushy, exhibits a compact growth habit, and forms fairly vigorous vegetation. The plant is well adapted to greenhouse forcing and to the low light and low humidity growing conditions commonly encountered in a home. Additionally, the plant is not particularly affected by crytogamic diseases.

1 Drawing Sheet

SUMMARY OF THE INVENTION

The new variety of Miniature rose plant was created by artificial pollination wherein two parents were crossed which previously had been studied in the hope that they would contribute the desired characteristics. The female parent (i.e., the seed parent) was the product of the pollination of the Anytime variety (non-patented in the United States) by the Meichanso variety (nonpatented in the United States). The Meichanso variety is sometimes known as the Parador variety. The male parent (i.e., the pollen parent) of the new variety was the Mogral variety (non-patented in the United States). The parentage of the new variety can be summarized as follows:

[Anytime × Meichanso] × Mogral.

The seeds resulting from the above pollination were sown and 47 plantlets were obtained which were physically and biologically different from each other. Selective study resulted in the identification of a single plant of the new variety.

It was found that the new variety of Miniature rose plant of the present invention possesses the following combination of characteristics:

(a) forms in abundance on a continuous basis attractive double long lasting blossoms which are rose bengal in coloration,
(b) forms fairly vigorous vegetation,
(c) exhibits a compact and bushy growth habit,
(d) is well adapted to greenhouse forcing and to the low light and low humidity growing conditions commonly encountered in the home, and
(e) is not particularly affected by crytogamic diseases.

The new variety well meets the needs of the horticultural industry for all usages. It is particularly well-suited for use as attractive ornamentation as a flowering pot plant for use indoors or outdoors.

The new variety has been found to undergo asexual propagation by a number of routes, including budding, grafting, cuttage, etc. The characteristics of the new variety have been found to be strictly transmissible by such asexual propagation from one generation to another.

The new variety has been named the Meiselgra variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety described herein were one year of age and were observed during February while growing on their own roots in greenhouses at Le Cannet des Maures, Var, France.

FIG. 1 illustrates a specimen of a young shoot;
FIG. 2 illustrates specimens of two floral buds before the opening of the sepals;
FIG. 3 illustrates specimens of two floral buds at the opening of the sepals;
FIG. 4 illustrates specimens of two floral buds at the opening of the petals;
FIG. 5 illustrates a specimen of two flowers in the course of opening;
FIG. 6 illustrates specimens of two fully open flowers — plan view — obverse;
FIG. 7 illustrates specimens of two fully open flowers — plan view — reverse;
FIG. 8 illustrates specimens of two fully open flowers immediately prior to petal drop — plan view — obverse;
FIG. 9 illustrates specimens of two fully open flowers immediately prior to petal drop — plan view — reverse;
FIG. 10 illustrates a specimen of a floral receptacle showing the arrangement of the stamens and pistils;
FIG. 11 illustrates a specimen of a floral receptacle showing the arrangement of the pistils (stamens removed);
FIG. 12 illustrates specimen of a flowering stem;
FIG. 13 illustrates a specimen of a main branch;
FIG. 14 illustrates specimens of two leaves with three leaflets with the upper surface being shown on the right and the under surface being shown on the left;
FIG. 15 illustrates specimens of two leaves with five leaflets with the upper surface being shown on the top right and the under surface being shown on the bottom left;

FIG. 16 illustrates specimens of two leaves with seven leaflets with the upper surface being shown on the top and the under surface being shown on the bottom; and FIG. 17 illustrates a specimen of a leaf with nine leaflets showing the upper surface.

DETAILED DESCRIPTION

Figures 1, 2, 3, 4, 5, 6, 7, 8, 9, 10, 11, 12, 13, 14, 15, 16, 17:
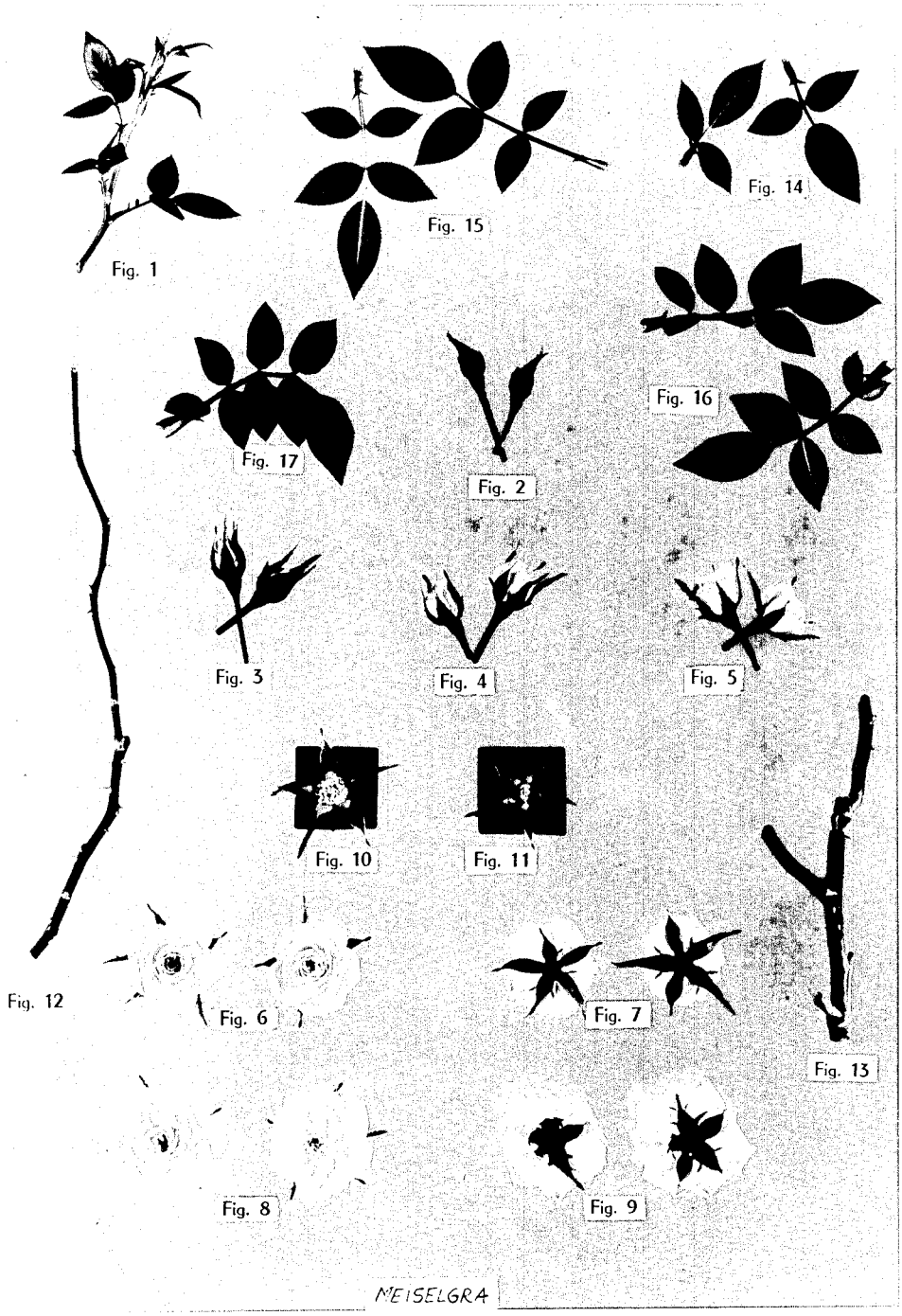

The chart used in the identification of the colors is that of The Royal Horticultural Society (R.H.S. Colour Chart). The terminology which precedes reference to the chart has been added to indicate the corresponding colors in common terms. The description is based on one year old specimens of the new variety during February while growing on their own roots in greenhouses at Le Cannet des Maures, Var, France.

Class: Miniature.

Plant:

*Height.*—Approximately 20 cm. on average above the pot when grown in 10 cm. pots.

*Habit.*—Bushy.

Branches:

*Color.*—Young stems: lettuce green, Yellow-Green Group 144A, more or less edged with reddish coloration. Adult wood: light green, Green Group 137C.

*Thorns.*—Size: small. Quantity: very few. Color: pinkish on young stems and greenish changing to tan on adult wood.

Leaves:

*Petioles.*—Upper surface: striped reddish brown on young foliage and medium green on adult foliage with more or less glandular edges. Under surface: light green with a few small prickles.

*Stipules.*—Adnate, pectinate, somewhat wide and linear.

*Leaflets.*—Number: 3, 5, 7 (most often), and 9. Sometimes the lower leaflet pair is incomplete. Shape: spearlike. Serration: single and regular. Texture: consistent. General appearance: fairly dense and semi-dull. Color (young foliage): Upper surface: lettuce green, Yellow-Green Group 144B, more or less edged with reddish coloration. Under surface: lettuce green, Yellow-Green Group 144B, more or less edged with reddish coloration. Color (adult foliage): Upper surface: dark green, Green Group 137A. Under surface: medium green, Green Group 138B.

Inflorescence:

*Number of flowers.*—Approximately 1 to 2 per stem.

*Peduncle.*—Straight, rigid, it bears a few pediculate glands, its length is approxiately 3.5 to 4 cm. on average.

*Sepals.*—Upper surface: tomentose and greenish in coloration. Under surface: medium green, the outer sepals have edges which are more or less glandular and slightly appendiculated.

*Buds.*—Shape: ovoid. Length: approximately 1.5 cm. on average. Size: small. Color upon opening: Upper surface: light rose bengal, Red-Purple Group 57C. Under surface: pale rose bengal, Red-Purple Group 57D.

*Flower.*—Form: cuplike and double. Diameter: approximately 3.5 cm. on average. Color (when opening begins): Upper surface: light rose bengal, Red-Purple Group 57C. Under surface: pale rose bengal, Red-Purple Group 57D. Color (when blooming): Upper surface: light rose bengal, Red-Purple Group 57C. Under surface: pale rose bengal, Red-Purple Group 57D. Color (at end of blooming): Upper surface: pale rose bengal, Red-Purple Group 57D. Under surface: pale rose bengal, Red-Purple Group 57D. Fragrance: none. Lasting quality: long. Petal number: approximately 39 to 42 on average. Petal form: outer petals tend to be rounded, and the inner petals tend to be oval. Petal texture: consistent. Petal drop: good. Anthers: normal, yellowish and located below the stigmas. Stamens number: approximately 44 on average. Filaments: greenish and of irregular heights. Pistil number: approximately 19 on average. Stigmas: straw colored and very frequently malformed. Styles: greenish-straw colored, of irregular heights. Receptacle: medium green, smooth and in longitudinal section it is pear-shaped.

Development:

*Vegetation.*—Fairly vigorous.

*Blooming.*—Abundant and continuous.

*Aptitude to bear fruit.*—Poor.

*Resistance to diseases.*—Good.

I claim:

1. A new and distinct variety of Miniature rose plant characterized by the following combination of characteristics:

(a) forms in abundance on a continuous basis attractive double long lasting blossoms which are bengal rose in coloration,
(b) forms fairly vigorous vegetation,
(c) exhibits a compact and bushy growth habit,
(d) is well adapted to greenhouse forcing and to the low light and low humidity growing conditions commonly encountered in the home, and
(e) is not particularly affected by crytogamic diseases;

substantially as herein shown and described.

* * * * *

MEISELGRA